United States Patent [19]

Eldridge, Jr.

[11] Patent Number: 4,596,329
[45] Date of Patent: Jun. 24, 1986

[54] PIVOTALLY MOUNTED SURGICAL INSTRUMENT HOLDER

[75] Inventor: John D. Eldridge, Jr., Newport Beach, Calif.

[73] Assignee: American Hospital Supply Corporation, Evanston, Ill.

[21] Appl. No.: 629,754

[22] Filed: Jul. 12, 1984

Related U.S. Application Data

[63] Continuation of Ser. No. 346,777, Feb. 8, 1982, abandoned.

[51] Int. Cl.⁴ ............................................. B65D 83/10
[52] U.S. Cl. .................................. 206/370; 206/63.3; 206/382; 206/818; 206/232; 206/470
[58] Field of Search ............... 206/44 R, 44.4, 232, 206/261, 262, 263, 363, 423, 366, 818, 379, 382, 380, 460, 470

[56] References Cited

U.S. PATENT DOCUMENTS

| | | | |
|---|---|---|---|
| 1,456,613 | 5/1923 | Bartels | 206/44.1 |
| 1,644,830 | 10/1927 | Henderson | 206/363 |
| 2,008,429 | 7/1935 | Weatherhead, Jr. | 206/232 |
| 2,403,825 | 7/1946 | Nissenbaum | 206/379 |
| 3,077,282 | 2/1963 | Eggers | 220/338 |
| 3,191,319 | 6/1965 | Waisgerber | 206/332 |
| 3,727,658 | 4/1973 | Zedridge, Jr. | 206/818 |
| 3,811,563 | 5/1974 | Fox, II | 206/461 |
| 4,167,230 | 9/1979 | Barratt | 206/380 |

FOREIGN PATENT DOCUMENTS

| | | | |
|---|---|---|---|
| 192843 | 12/1956 | Fed. Rep. of Germany | 206/460 |
| 595910 | 9/1959 | Italy | 206/818 |

Primary Examiner—Joseph Man-Fu Moy
Attorney, Agent, or Firm—Donald L. Barbeau

[57] ABSTRACT

A surgical instrument container has a top and bottom whose opposing surfaces are bordered by sidewalls and articulately connected to form an enclosed box. A planar substrate having upper and lower surfaces adapted to receive surgical instruments is pivotally mounted between the top and bottom. When the box is open, the substrate can be pivoted between the top and bottom to provide easy access to both upper and lower substrate surfaces. The substrate is positioned within the sidewalls of the top and bottom surfaces to effect enclosure of the substrate when the box is closed and thereby prevent retained surgical instruments from protruding through or falling out of the box. The substrate may be a porous foam or magnetic material or combination of each. The box may be mechanically or magnetically latched. The box may be composed of transparent material to permit visual inspection of the retained instruments when the box is closed.

4 Claims, 14 Drawing Figures

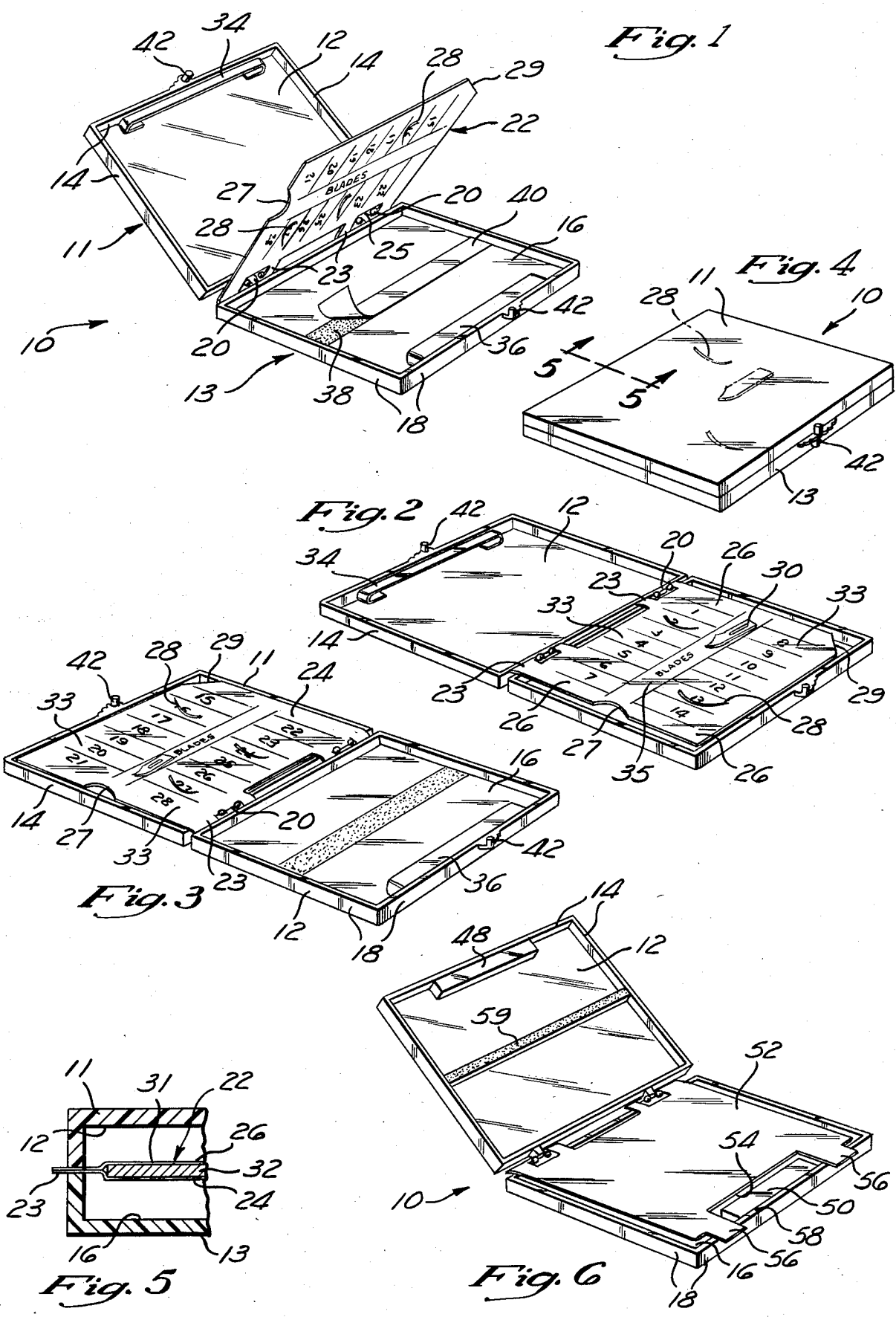

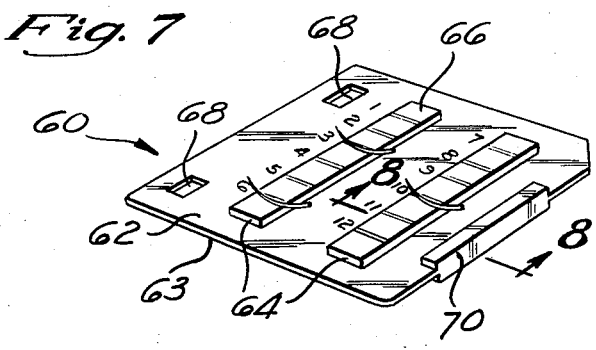
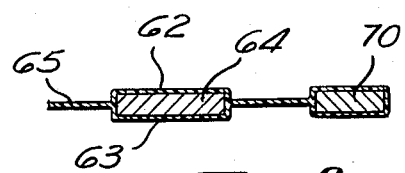
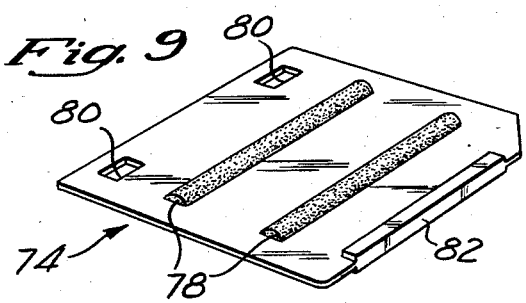
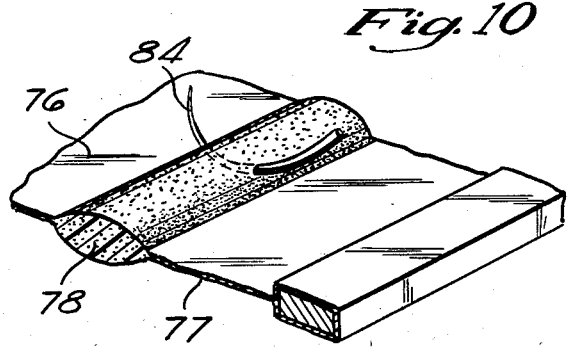
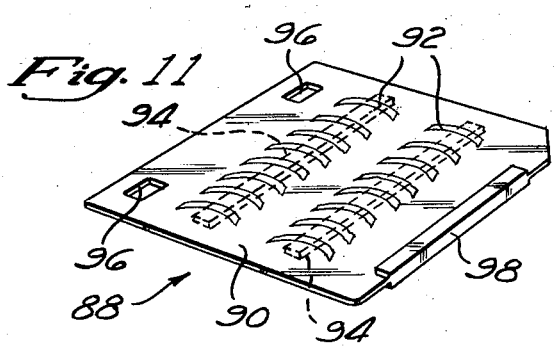
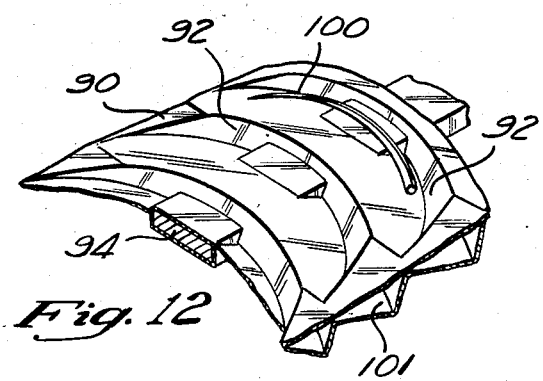
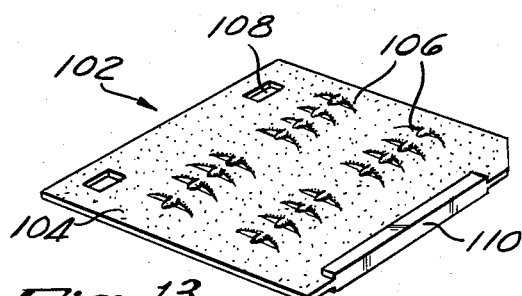
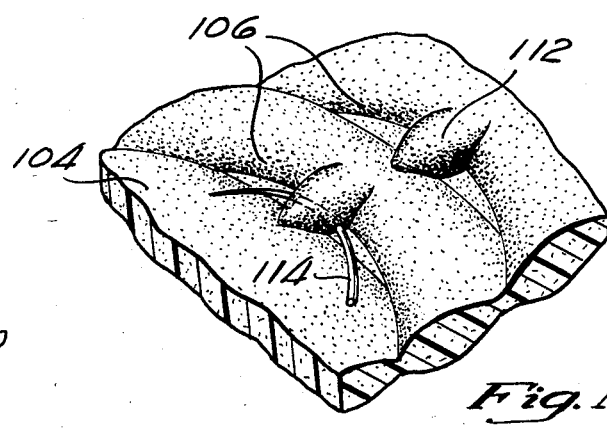

PIVOTALLY MOUNTED SURGICAL INSTRUMENT HOLDER

This application is a continuation, of application Ser. No. 346,777, filed Feb. 8, 1982 abandoned.

BACKGROUND OF THE INVENTION

The invention is directed to holders for surgical instruments and more specifically to holders which securely encase such instruments prior to disposal thereof.

Virtually every surgical procedure requires the use of small, sharp inplements such as suture needles, blades, staples, knives and the like. These instruments which are utilized in a sterile condition must be placed on a readily accessible sterile retainer during an operation to maintain the sterility of the operating area.

Secondly, instruments, such as needles, require a system for providing a strict and accurate accountability for each implement used. Thus, the operating nurse must have a reliable system for precisely determining how many instruments were used in surgery and for insuring that all such instruments have been accounted for before surgical closure of the patient.

Finally, many of these instruments are disposable and there is therefore a need for a safe, effective means to discard the instruments which may be contaminated with bacteria or virus after surgery without risking injury to operating room personnel.

Several disposable surgical instrument holders have been developed in the past. For example, U.S. Pat. No. 3,727,658 to Eldridge discloses a receiver for implements utilizing a plurality of magnets which are secured to the surface of a foldable, foamed, elastomeric backing sheet. U.S. Pat. No. 4,008,802 to Freitag discloses a needle retainer formed of a pad of resilient material having upstanding ridges through which needles are inserted. Each needle receiving zone is consecutively numbered to provide a method for maintaining an accurate count of the number of needles utilized during a surgical procedure. Although such devices are quite useful, the sharp instruments are exposed at the lateral edges of the devices when they are in a folded disposable condition. This is undesirable since the instruments may become detached and fall out of the device or possibly pierce or protrude through the assembly.

Attempts have been made to solve this problem by providing receivers which completely enclose the instruments. For example, U.S. Pat. No. 4,013,109 to Sandel discloses a disposable container formed from a non-deformable casing which has magnetic sheets covering the entire surfaces of both the upper and lower portions of the case. Although the instruments are enclosed, the container does not provide a count system for the sharp instruments, nor does it allow for visual inspection of the implements after the container is closed. U.S. Pat. No. 4,167,230 attempts to alleviate this problem by providing a transparent tray having a bottom whose upper surface is adapted to receive the surgical instruments. The cover of the tray nests above the bottom half and securely encloses the receiver. Although an improvement in some respects, the device provides only a solitary receiving surface. Such a device has a low instrument holding capacity. Since the devices are disposable, it is critical that they be manufactured and sold at low cost and provide the maximum implement holding capacity possible.

There is therefore a definite need for a device which completely encases the implements, provides an accurate counting system and permits viewing of the implements when the device is in its disposable configuration. Moreover, the device must provide maximum holding capacity and be manufactured at low cost.

SUMMARY OF THE INVENTION

The disclosed invention is a surgical instrument container having a top and bottom whose opposing surfaces are bordered by sidewalls. A substrate having upper and lower surfaces adapted to receive surgical instruments is located between the top and bottom. The top, substrate and bottom are articulately connected along a common hinge line and are movable between open and closed positions. In the closed position, the top and bottom form an enclosed box which completely encases instruments retained by the substrate. In the open position, the top and bottom are spaced to allow the substrate to be pivoted back and forth between them. This allows easy access to both surfaces of the substrate and permits both sides of the substrate to retain implements.

The substrate can take a variety of implement receiving configurations. In general, the substrate may contain magnets to magnetically hold the implements or be a porous foam which is pierced by the sharp implements to provide retention. In one preferred embodiment, the substrate is a planar magnet which has numbered needle receiving areas to provide a system to accurately count each instrument used. The top and bottom surfaces of the box may also be adapted to retain surgical implements.

Thus, the unique structure of the pivotally mounted substrate produces a container which has four potential implement receiving surfaces. This large implement receiving capacity is provided in an uncomplicated device which requires no more volume than the size of the box. Moreover, the substrate is completely encased within the box to prevent instruments from falling out. The box is advantageously formed of rigid material to prevent sharp instruments from piercing through the exterior.

The box may be mechanically or magnetically latched. In a preferred embodiment, each of the top and bottom surfaces has a magnetizable member mounted thereon, at least one of the members being magnetized. The members are positioned to be in mutual contact when the box is closed to magnetically secure the box.

If a mechanical latch is employed with a planar magnetic substrate, magnetizable members may be affixed to the top and bottom surfaces to hold the substrate against the top or bottom surface.

These and other advantages of the invention will be clarified in the discussion below with reference to the drawings in which:

FIG. 1 is a perspective view of the box in its open position with the substrate pivotally mounted between the top and bottom;

FIG. 2 is a perspective view of the box of FIG. 1 in its fully opened position showing the substrate held against the bottom by a magnetic strip;

FIG. 3 is a perspective view of the box of FIG. 1 in its fully opened position showing the substrate held against the top by a magnetic strip;

FIG. 4 is a perspective view of the box in its closed position;

FIG. 5 is a fragmentary sectional view of the box taken through line 4—4 of FIG. 4 showing the hinge area;

FIG. 6 is a perspective view of an alternate embodiment of the box and substrate of FIG. 1 showing a magnetic latch;

FIG. 7 is a perspective view of a second alternate embodiment of an implement receiving substrate;

FIG. 8 is a sectional view of the second alternate substrate taken through line 7—7 of FIG. 7;

FIG. 9 is a perspective of a third alternate embodiment of an implement receiving substrate;

FIG. 10 is an enlarged fragmentary perspective view of the third alternate substrate;

FIG. 11 is a perspective view of a fourth alternate embodiment of an implement receiving substrate;

FIG. 12 is an enlarged fragmentary perspective view of the fourth alternate substrate;

FIG. 13 is a perspective view of a fifth alternate embodiment of an implement receiving substrate; and FIG. 14 is an enlarged fragmentary perspective view of the fifth alternate substrate.

DETAILED DESCRIPTION OF THE PREFERRED EMBODIMENT

Referring to FIG. 1, a surgical instrument holding device 10 is shown having a top 11 and a bottom 13. The top 11 is formed by a top surface 12 having four sides which are bordered by four sidewalls 14. The bottom 13 is formed by a bottom surface 16 which has four sides which are bordered by four sidewalls 18. The top 11 and bottom 13 are an essentially equal size and shape and are articulately connected between adjacent sidewalls by two hinges 20. The hinges 20 may be of any suitable type which permits the top 11 and the bottom 13 to pivot with respect to each other.

An elongate magnetizable strip 34 is mounted upon the top surface 12 adjacent to one of the sidewalls 14. Similarly, a magnetizable strip 36 is positioned adjacent to one of the bottom sidewalls 18 and is affixed to the bottom surface 16. The strips 34, 26 may be affixed by an adhesive or any other suitable means.

Pivotally mounted between the top surface 12 and the bottom surface 16 is a planer substrate 22. Referring to FIGS. 1, 2, 3 and 5 the substrate 22 is essentially rectangular. One side has a pair of laterally spaced extensions 23 which each have an opening 25 extending therethrough. The openings 25 are bordered on each side by the substrate 22 forming a rectangularly shaped slot. In addition, another side of the substrate 22 has a recess or notch 27 and one corner 29 is chamfered. The substrate 22 is formed of a thin coating material 31 which envelops a planar magnet 32. The material 31 can be elastomeric, cloth, paper or other suitable material. The material 31 prevents magnetic dust from entering the area of surgery and also may be chosen to provide support to the magnet 32 to prevent it from bowing.

The coating material 31 of the substrate 22 has a lower surface 24 and an upper surface 26 which are adapted to receive surgical instruments. In a preferred embodiment each surface 24, 26 is identical and has two columns of sequentially numbered instrument receiving zones 33 which are divided by a blade receiving zone 35. Since the substrate 22 is composed of a planar magnet, it will magnetically hold magnetizable instruments such as needles, blades, knives, and the like. Thus, in FIGS. 1 and 2, surgical needles 28 are shown retained in several of the numbered zones 33. The zones 33 allow operating room personnel to accurately account for every needle used in a surgical operation. In FIG. 2 a blade 30 is shown retained in the blade receiving zone 35.

The substrate 22 is pivotally mounted to the top surface 12 and the bottom surface 16 by positioning the hinges 20 within the openings 25. The top 11, the bottom 13 and the substrate 22 have a common hinge line. When the device 10 is in its open position, the substrate 22 is free to move articulately back and forth between the top surface 12 and the bottom surface 16. The recess 27 or chamfered corner 29 provide space for the finger so that the substrate 22 can be easily grasped and pivoted between the top and bottom surfaces 12, 16.

Referring to FIGS. 2 and 3 the device 10 is shown in its fully open position. As shown in the drawings, the hinges 20 extend from one marginal edge of the hinged side of the box further than any other part thereof, to permit the box to be fully opened, with the top surface 12 and the bottom surface 16 essentially co-planar. In order to utilize both the upper surface 26 and lower surface 24 of the substrate 22 as implement receivers, the substrate 22 is pivoted between the top surface 12 and the bottom surface 16. In a first position shown in FIG. 2, the substrate 22 is located above and essentially parallel to the bottom surface 16. In this first position, the upper surface 26 is exposed and oriented upward to permit the placement of surgical instruments, such as the blade 30, on the substrate 22. The substrate 22 is held in its first position by the magnetizable strip 36. The strip 36 also spaces the substrate 22 above the bottom surface 16. A space is therefore created between the lower surface 24 of the substrate 22 and the bottom surface 16 of the box. This space is of a sufficient size to accommodate the needles 28 or other surgical instruments which may be attached to the lower surface 24 of the substrate 22.

In order to expose the lower surface 24 of the substrate 22, the substrate 22 can be pivotally moved from its first position shown in FIG. 2 to a second position shown in FIG. 3 in which the substrate 22 is located above the parallel to the upper surface 12. In this second position, the magnetizable strip 34 holds the substrate 22 and provides a spacing between the upper surface 26 of the substrate 22 and the top surface 12. This space is of a sufficient size to permit surgical implements, such as the blade 30, to be retained on the upper surface 26. Thus, the unique structure of the pivotally mounted substrate 22 allows the device 10 to provide at least two implement receiving surfaces 24, 26 which are easily accessible to operating room personnel when the device 10 is in its opened position.

Referring again to FIG. 1, an optional adhesive strip 38 is shown affixed to the bottom surface 16. The strip 38 is covered by a peel-away strip 40 made of a paper material as is well known to those in the art. Thus, by peeling away the paper strip 40, the adhesive 38 is exposed and can be used to retain additional surgical instruments. Both the top surface 12 and the bottom surface 16 have a mechanical latch element 42 which mechanically latches the box in its closed position.

It should be understood that a plurality of implement receiving substrates may be used. Thus, the box could contain multiple tiers of pivotally mounted substrates to even further increase the implement holding capacity of the device.

Referring to FIG. 4, the device 10 is shown in its closed position mechanically latched by the elements 42 in a known manner. Advantageously, the top and bottom 11, 13 are made of a transparent material. This permits the visual inspection of surgical implements, such as the blade 30, retained on the substrate 22 when the device 10 is closed. Also advantageously, the top and bottom 11, 13 are made of a rigid material, such as a hard plastic which prevents the sharp implements retained on the substrate 22 from piercing or projecting through the exterior of the device 10. As shown in FIG. 4, when the device 10 is closed, the top and bottom sidewalls 14, 16 mutually interface to provide a completely enclosed container. Thus, the needles 28 and the blades 30 are encapsulated within the device 10 and cannot fall out.

Referring to FIG. 5, the device 10 is shown in its closed position with the substrate 22 lying parallel to the top and bottom surfaces 12, 16. The substrate 22 is spaced from the top and bottom surfaces 12, 16 an approximately equal distance providing ample room to encase instruments on either side of the substrate 22.

Referring to FIG. 6, an alternate embodiment of the device 10 is shown. The top surface 12 has a magnetizable member 48 affixed thereto and located adjacent to the top sidewall 14. Similarly, the bottom surface 16 has affixed thereto a magnetizable member 50 which is located adjacent to a corresponding bottom sidewall 18. The magnetizable members 48, 50 are of a sufficient height and are positioned so that they will be in mutual contact when the device 10 is closed. At least one of the magnetizable members 48, 50 is magnetized so that when the members 48 and 50 are placed in mutual contact, they will magnetically lock the top and bottom surfaces 12, 16 together. The members 48, 50 therefore are an alternative to the mechanical latching elements 42.

A planar substrate 52 has a slot 54 cut into one edge. The slot 54 is of sufficient size to permit full exposure of the magnetizable member 50 when the substrate 52 is parallel to the bottom surface 16. Similarly, the slot 54 will permit full exposure of the magnetizable member 48 when the substrate 52 is pivoted to be parallel to the top surface 12. Thus, the slot 54 permits the magnetizable members 48, 50 to contact each other when the device 10 is closed.

The substrate 52 has a pair of tabs 56 which protrude outward exterior of the bottom sidewall 18. The tabs 56 therefore rest against an upper edge 58 of the bottom sidewall 18 to support and maintain the substrate 52 in a parallel position with respect to the bottom surface 16. The tabs 56 are very thin so that the top and bottom sidewalls 14, 18 substantially engage when the device 10 is closed. Thus, the tabs 56 do not prevent the device 10 from completely encasing the portion of the substrate 52 which receives the surgical instruments. Were it not for the tabs 56, the magnet in substrate 52 would tend to flex against the bottom surface 16 which could result in implements being dislodged from the substrate. In addition, the tabs 56 provide a convenient handle for the operator's finger to aid in pivoting the substrate 52.

An optional strip of foam 59 is shown affixed to the upper surface 12 extending between opposing top sidewalls 14. The height of the foam is approximately that of the height of the top sidewalls 14. The foam 59 can be used to hold sharp surgical instruments which are placed through the foam. In addition, the foam 59 maintains the substrate 52 spaced from the top surface 12. Thus, if a similar piece of foam were placed on the bottom surface 16, the need for the tabs 56 would be eliminated.

Referring to FIGS. 7 and 8 a second alternate embodiment 60 for the implement receiving substrate 22 is shown. The substrate 60 is quite similar to the receiver for surgical instruments disclosed in U.S. Pat. No. 3,727,658, issued to the instant inventor, John D. Eldridge, Jr., which is herein incorporated by reference. The substrate 60 has an upper surface 62 and a lower surface 63 formed by a thin elastomeric material 65. The material 65 envelops two bar magnets 64 thereby preventing magnetic dust from entering the surgical area. Each of the bar magnets 64 has numbered needle instrument receiving zones 66 which provide an accurate system for counting the surgical implements which have been used during a surgical procedure. The substrate 60 has a pair of slots 68 sized to fit over the hinges 20 of the device 10. The material 65 also envelops an additional magnet 70 which is positioned along one edge of the substrate 60. The magnet 70 contacts the magnetizable members 34, 36, thereby holding the substrate 60 in a position parallel to, but spaced from the top surface 14 or the bottom surface 16. Thus, the substrate 60 provides two identical implement receiving surfaces 62, 63 which are made accessible by pivotally mounting the substrate 60 over the hinges 20 between the top and bottom surfaces 12, 16.

Referring to FIGS. 9 and 10, a third alternate embodiment 74 of the substrate 22 is shown. The substrate 74 is quite similar to a receiver for surgical instruments as disclosed in U.S. patent application Ser. No. 006,732 filed Jan. 26, 1979 by the instant inventor, John D. Eldridge, Jr., which is herein incorporated by reference. The substrate 74 is composed of a porous foam which has an upper surface 76 and a lower surface 77. Extending outward from the upper and lower surfaces 76, 77 are a pair of elongate embossments 78. The substrate 74 also has a pair of slots 80. Positioned along one edge of the substrate 74 is a magnet 82 serving the same function as the magnet 68 in FIG. 6. In FIG. 10 a needle 84 is shown extending through the foamed embossment 78 above the upper surface 76. It will be understood that the upper and lower surfaces 76, 77 are virtually identical. Thus, the substrate 74 also has two surgical receiving surfaces. It should be understood that the foamed substrate could be made of various types of foam having different degrees of rigidity. Less rigid foams may require a rigidizing supporting member between the upper and lower surfaces 76, 77 to prevent deformation. The magnet 82 holds the substrate 74 against the magnetizable strips 34, 36. The slots 80 fit over the hinges 20 to pivotally mount the substrate 74 between the top and bottom surfaces 12, 16.

Referring to FIG. 11, a fourth alternate embodiment 88 of the substrate 22 is shown. The substrate 88 is substantially similar to a surgical receiver disclosed in U.S. patent application Ser. No. 006,732 by the instant inventor, John D. Eldridge, Jr., filed contemporaneously herewith and which is herein incorporated by reference. The substrate 88 has an upper surface 90 formed of a thin elastomeric material which has two columns of crescent-like depressions 92. Extending somewhat above and through the middle of each column of depressions 92 is a bar magnet 94 which lies beneath the elastomeric material of the surface 90. The substrate 88 also has a pair of slots 96. Located along one edge of the substrate 88 is a bar magnet 98. In combination with the device 10, the slots 96 pivotally mount the substrate 88 over the hinges 20. The magnet 98 holds the substrate 88 against the magnetizable strips 34, 36.

Referring to FIG. 12, the precise configuration of the column of crescent-shaped depressions 92 is shown. The bar magnet 94 extends somewhat above the depth of the depressions and holds surgical instruments, such as a needle 100 within each crescent-shaped depression. It should be understood that the substrate 88 has a lower surface 101 which is substantially identical to the upper surface 90. Thus, the substrate 88 has two surfaces for receiving surgical instruments.

Referring to FIG. 13, a fifth alternate embodiment 102 of the substrate 22 is shown. The substrate 102 is substantially similar to a receiver for surgical implements disclosed in U.S. patent application Ser. No. 006,732 by the instant inventor, John D. Eldridge, Jr., filed contemporaneously herewith which is herein incorporated by reference. The substrate 102 is composed of a porous foam having an upper surface 104. The surface 104 has two columns of crescent-shaped depressions 106. The substrate 102 has a pair of slots 108. Along one edge of the substrate 102 is located a bar magnet 110. When employed with the device 10, the substrate 102 is pivotally mounted over the hinges 20 by means of the slots 108. The magnet 110 holds the substrate 102 against the magnetizable members 34, 36.

Referring to FIG. 14, a portion of the column of crescent-shaped depressions 106 is shown. Each depression has a centrally located tapered embossment 112 which receives a surgical implement such as a needle 114. The depressions are formed to partially envelop an implement. This reduces the chance that a needle will become detached from the substrate. The embossments 112 are tapered to receive different sized needles. Thus, the wide area of the embossment 112 holds a large needle whereas the narrow area holds a small needle. This aspect is important in making sure the needle will lie flat against the substrate as shown in FIG. 14 rather than protruding upward. Finally, it should be understood that the lower surface of the substrate 102 (not shown) is virtually identical to the surface 104 so that the substrate 102 has two implement receiving sides. As discussed above with respect to the substrate 74, it may be necessary, when utilizing softer foams, to employ a rigid support member between the upper and lower surfaces 102, 104.

It should be understood that, in addition, substrates like any of 22, 52, 60, 74, 88 or 102 could be affixed to either the top surface 12 or bottom surface 16. Thus, the top and bottom surfaces 12, 16 can also be adapted to receive surgical implements. The device 10, therefore, has a potential of four surgical implement receiving surfaces: One provided by the top surface 12, a second provided by the bottom surface 16 and a third and fourth surface provided by the pivotally mounted substrate. The invention, therefore, offers a large instrument receiving capacity contained in a relatively small volume. In addition, the device is uncomplicated and can be easily manufactured at low cost.

What is claimed is:

1. A surgical instrument container comprising:
    a top planar surface bordered by sidewalls having marginal edges;
    a bottom planar surface bordered by sidewalls having marginal edges, said top and bottom surfaces being articulately connected to form a box having open and closed positions wherein marginal edges of said top and bottom surfaces are disposed adjacent each other when the box is in a closed position;
    a hinge for opening and closing said box, said hinge connecting respective adjacent marginal edges of said top and bottom surfaces along a hinge line on one side of said box, so that said top and bottom surfaces can pivot relative to each other about said hinge line, said hinge extending beyond said one side of said box further than any other part thereof to permit said box to be fully opened with said planar surfaces of said containers essentially coplanar;
    a substrate disposed within said box and having upper and lower surfaces adapted to retain surgical instruments;
    said substrate being pivotally connected to said box between said top and bottom surfaces to encapsulate instruments held by said substrate within the box when said box is in the closed position, said substrate being articulately connected to said box to permit said substrate to freely pivot essentially 180° between first and second instrument receiving positions when the box is open to provide easy access to both upper and lower surfaces;
    said substrate being positioned above and essentially parallel to the top surface when in the first position, and being located above and essentially parallel to the bottom surface when in the second position;
    said substrate upper surface being positioned to receive instruments in the first position and said substrate lower surface being positioned to receive instruments in the second position;
    a hinge on said substrate for pivotally mounting said substrate along said one side of said box, said hinge having a portion thereof disposed between said marginal edges of said upper and lower surfaces forming said box when said box is in the closed position, and a portion which extends outside of said box when said box is in either- in the open or closed position;
    said substrate hinge and said box hinge being hinged along a common hinge line extending beyond said one side of said box, wherein said substrate hinge comprises a slot formed in said substrate along one edge thereof so that said box hinge passes through said slot to mount said substrate within the box; and
    a means on said substrate for pivoting the substrate between the first and second instrument receiving positions so that the substrate may lie against either of said surfaces to selectively expose surgical instruments on either side of said substrate and permit access thereto.

2. The instrument container of claim 1 wherein said top and bottom surfaces are formed of essentially transparent material to permit visual inspection of said upper and lower substrate surfaces when the box is in a closed position.

3. The instrument container of claim 1 wherein said pivoting means comprises a tab extending from the edge of said substrate and extending outside of said box when said box is in the closed position.

4. A surgical instrument container comprising:
    a top planar surface formed of essentially transparent material bordered by sidewalls having marginal edges;
    a bottom surface formed of essentially transparent material bordered by sidewalls having marginal edges, said top and bottom surfaces being articulately connected to form a box having open and closed positions wherein marginal edges of said top and bottom surfaces are disposed adjacent each other when the box is in a closed position;

a pair of hinges for opening and closing said box, said hinges connecting respective adjacent marginal edges of said top and bottom surfaces along a hinge line on one side of said box, so that said top and bottom surfaces can pivot relative to each other about said hinge line, said hinges extending beyond said one side of said box further than any other part thereof to permit said box to be fully opened with said planar surfaces of said containers essentially coplanar;

a substrate disposed within said box and having upper and lower surfaces adapted to retain surgical instruments on a foamed embossment;

said substrate being pivotally connected to said box between said top and bottom surfaces to encapsulate instruments held by said substrate within the box when said box is in the closed position, said substrate being articulately connected to said box to permit said substrate to freely pivot essentially 180° between first and second instrument receiving positions when the box is open to provide easy access to both upper and lower surfaces;

said substrate being positioned above and essentially parallel to the top surface when in the first position, and being located above and essentially parallel to the bottom surface when in the second position;

said substrate upper surface being positioned to receive instruments in the first position and said substrate lower surface being positioned to receive instruments in the second position;

a hinge on said substrate for pivotally mounting said substrate along said one side of said box, said hinge having a portion thereof disposed between said marginal edges of said upper and lower surfaces forming said box when said box is in the closed position, and a portion which extends outside of said box when said box is in either in the open or closed position;

said substrate hinge and said box hinges being hinged along a common hinge line extending beyond said one side of said box, wherein said substrate hinge comprises a pair of slots formed in said substrate along one edge thereof so that said box hinge pass through said slots to mount said substrate within the box; and a tab on said substrate for pivoting the substrate between the first and second instrument receiving positions so that the substrate may lie against either of said surfaces to selectively expose surgical instruments on either side of said substrate and permit access thereto, said tab extending from the edge of said substrate and extending outside of said box when said box is in the closed position.

* * * * *